(12) United States Patent
Evans et al.

(10) Patent No.: US 8,357,812 B2
(45) Date of Patent: Jan. 22, 2013

(54) PROCESS FOR PREPARING A REJUVENATED EPOXIDATION CATALYST

(75) Inventors: Wayne Errol Evans, Richmond, TX (US); Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/613,849

(22) Filed: Dec. 20, 2006

(65) Prior Publication Data

US 2007/0167639 A1 Jul. 19, 2007

Related U.S. Application Data

(60) Provisional application No. 60/752,977, filed on Dec. 22, 2005.

(51) Int. Cl.
*C07D 301/10* (2006.01)
(52) U.S. Cl. .......... 549/534; 549/536; 549/537; 502/24; 502/347
(58) Field of Classification Search .................. 549/536, 549/534, 537; 502/34, 347, 348, 24
See application file for complete search history.

(56) References Cited

U.S. PATENT DOCUMENTS

| | | | |
|---|---|---|---|
| 3,518,285 A | 6/1970 | Fenton et al. | 260/348.5 |
| 4,033,903 A | 7/1977 | Maxwell | 252/476 |
| 4,125,480 A | 11/1978 | Maxwell | 252/414 |
| 4,186,106 A | 1/1980 | Rebsdat et al. | 252/414 |
| 4,278,562 A | 7/1981 | Mross et al. | 252/430 |
| 4,324,699 A | 4/1982 | Mross et al. | 252/463 |
| 4,361,504 A | 11/1982 | Solomon et al. | 252/463 |
| 4,366,092 A | 12/1982 | Winterton | |
| 4,491,638 A | 1/1985 | Busse | 502/167 |
| 4,808,738 A | 2/1989 | Lauritzen | 549/536 |
| 4,810,689 A * | 3/1989 | Hayden | 549/534 |
| 5,187,140 A | 2/1993 | Thorsteinson et al. | 502/348 |
| 5,384,418 A | 1/1995 | Zajacek et al. | 549/531 |
| 5,618,954 A | 4/1997 | Boeck et al. | 549/534 |
| 5,905,161 A | 5/1999 | Boeck et al. | 549/534 |
| 6,380,119 B1 | 4/2002 | Grosch et al. | 502/49 |
| 6,455,713 B1 | 9/2002 | Monnier | 549/536 |
| 6,710,002 B2 | 3/2004 | Grosch et al. | 502/49 |
| 7,102,022 B2 | 9/2006 | Evans et al. | 549/536 |
| 2004/0236124 A1 * | 11/2004 | Evans et al. | 549/534 |

FOREIGN PATENT DOCUMENTS

| | | |
|---|---|---|
| CA | 1165264 | 4/1984 |
| DE | 258514 A3 | 7/1988 |
| DE | 288055 A * | 3/1991 |
| DE | 288055 A7 | 3/1991 |
| EP | 0211521 | 3/1990 |
| EP | 568407 | 11/1993 |
| EP | 0918762 | 5/2001 |
| EP | 1073649 | 9/2003 |
| EP | 1283747 | 3/2004 |
| EP | 1115484 | 6/2004 |
| EP | 1426106 | 6/2004 |
| EP | 1314473 | 3/2007 |
| GB | 1413251 | 11/1975 |
| WO | WO9617811 | 6/1996 |
| WO | WO9800413 | 1/1998 |
| WO | WO9800414 | 1/1998 |
| WO | WO9800415 | 1/1998 |
| WO | WO0015332 | 3/2000 |
| WO | WO0141926 | 6/2001 |
| WO | WO2004101144 | 11/2004 |
| WO | WO2005097318 | 10/2005 |
| WO | WO2006102189 | 9/2006 |

OTHER PUBLICATIONS

Cowell, J.J. et al, Ultraselective Epoxidation of Butadiene on Cu{111} and the Effects of Cs Promotion, Journal of the American Chemical Society, 2000, pp. 2381-1382.
Monnier, J.R. et al, Stability and Distribution of Cesium in Cs-Promoted Silver Catalysts Used for Butadiene Epoxidation, Journal of Catalysis, 226 (2004); pp. 401-409.
Monnier, J.R. et al, Effects of Chlorine and Chlorine Dynamics During Silver-Catalyzed Epoxidation of Butadiene, Journal of Catalysis, 226 (2004); pp. 321-333.
Dioos, B.M.L. et al, $Cr^{III}$ (Salen) Impregnated on Silica for Asymmetric Ring Opening Reactions and its Recovery Via Desorption/re-Impregnation, Tetrahedron Letters 44 (2003); pp. 8815-8817.

* cited by examiner

*Primary Examiner* — Melvin C Mayes
*Assistant Examiner* — Stefanie Cohen (57) ABSTRACT

A process for preparing a rejuvenated epoxidation catalyst, for the epoxidation of one or more olefins using the rejuvenated epoxidation catalyst to produce olefin oxide, and for the production of a 1,2-diol, a 1,2-diol ether, or an alkanol amine from the olefin oxide, the process comprising: providing a quantity of spent epoxidation catalyst having a cumulative alkylene oxide production of 0.16 $kT/m^3$ of the spent epoxidation catalyst or more; and, depositing additional silver on the spent epoxidation catalyst in an amount of 0.2% w or more, based on the weight of the spent epoxidation catalyst.

31 Claims, 2 Drawing Sheets

PROCESS FOR PREPARING A REJUVENATED EPOXIDATION CATALYST

CROSS-REFERENCE OF RELATED APPLICATION

This application claims the benefit of U.S. Provisional Application No. 60/752,977 filed Dec. 22, 2005 the entire disclosure of which is hereby incorporated by reference.

FIELD OF THE INVENTION

The present application relates to a process for preparing a rejuvenated epoxidation catalyst. The application also relates to a process for epoxidation of one or more olefins using the rejuvenated epoxidation catalyst. The application also relates to a process of using olefin oxide produced by the epoxidation to produce a 1,2-diol, a 1,2-diol ether, or an alkanol amine.

BACKGROUND OF THE INVENTION

Ethylene oxide and other olefin oxides are important industrial chemicals used as a feedstock for making such chemicals as ethylene glycol, propylene glycol, ethylene glycol ethers, ethylene carbonate, ethanol amines and detergents. One method for manufacturing an olefin oxide is by olefin epoxidation, that is the catalyzed partial oxidation of the olefin with oxygen yielding the olefin oxide.

In olefin epoxidation, a feed containing the olefin and oxygen is passed over a bed of catalyst contained within a reaction zone that is maintained at certain reaction conditions. The epoxidation catalyst generally contains the catalytically active species, typically a Group 11 metal (in particular silver) and promoter components, on a shaped carrier material.

During the epoxidation, the catalyst is subject to a performance decline, which represents itself by a loss in activity of the catalyst and selectivity in the formation of the desired olefin oxide. In response to the loss of activity, the epoxidation reaction temperature may be increased such that the production rate of the olefin oxide is maintained. The operation of commercial reactors is normally limited with respect to the reaction temperature. When the applicable temperature limit has been reached, either the production rate of the olefin oxide is reduced or the production of the olefin oxide has to be interrupted for an exchange of the existing charge of epoxidation catalyst for a fresh charge.

U.S. Pat. No. 4,529,714 (the "'714 patent") describes a process for regenerating silver containing carrier catalysts used in the preparation of ethylene oxide. The process comprises treating a deactivated catalyst with a solution comprising a potassium, rubidium, or cesium compound and a reducing agent. In the Example of the '714 patent, an ethylene oxide catalyst was regenerated after approximately four years of service, during which the "catalytic activity" (i.e., selectivity) diminished from an initial 81.5 percent (at 218° C.) to 76.7 percent (at 247° C.). '714 patent, col. 4, 11. 16-18; see also Table spanning col. 3-4. The maximum increase in "S %" reflected in that Table at any temperature is only 3.2% (an increase from 76.7 to 79.9).

To a large extent, the selectivity of an epoxidation catalyst determines whether an epoxidation process is economically attractive. For example, a one percent improvement in the selectivity of an epoxidation process can produce a substantial reduction in the yearly operating cost of a large scale ethylene oxide plant.

A need exists for processes for producing rejuvenated epoxidation catalyst with greater selectivity and/or greater activity.

SUMMARY OF THE INVENTION

The present application provides a process of rejuvenating a spent epoxidation catalyst to produce a rejuvenated epoxidation catalyst having greater selectivity and/or greater activity than the spent epoxidation catalyst.

In one embodiment, the invention provides a process for preparing a rejuvenated epoxidation catalyst, the process comprising: providing a quantity of spent epoxidation catalyst having a cumulative alkylene oxide production of 0.16 kilotons ("kT")/$m^3$ of the spent epoxidation catalyst or more; and, depositing additional silver on the spent epoxidation catalyst in an amount of 0.2% w or more, based on the weight of the spent epoxidation catalyst.

In one embodiment, the invention provides a process for the epoxidation of one or more olefins comprising reacting a feed comprising one or more olefins in the presence of a rejuvenated epoxidation catalyst prepared according to this invention.

In another embodiment, the invention provides a process for the production of a 1,2-diol, a 1,2-diol ether, or an alkanol amine, the process comprising converting an olefin oxide into the 1,2-diol, the 1,2-diol ether, or the alkanol amine wherein the olefin oxide has been obtained by a process for the epoxidation of one or more olefins in the presence of a rejuvenated epoxidation catalyst prepared according to this invention.

DETAILED DESCRIPTION OF THE INVENTION

The present application provides a process for rejuvenating spent epoxidation catalyst to produce rejuvenated epoxidation catalyst which exhibits increased selectivity.

In one embodiment, the application provides a process for rejuvenating spent epoxidation catalyst to produce rejuvenated epoxidation catalyst which exhibits increased activity.

In one embodiment, the rejuvenation process produces rejuvenated epoxidation catalyst which exhibits both increased selectivity and increased activity.

The rejuvenation process advantageously can reduce the need to dispose of used carrier material and/or dopant, thereby reducing disposal and environmental costs.

The rejuvenation process advantageously can increase the profitability of an epoxidation process by reducing the need for and the cost of obtaining fresh carrier material.

Another advantage of the rejuvenation process is that it is not necessary to incur the cost to recover silver from the spent epoxidation catalyst.

Rejuvenation of Spent Epoxidation Catalyst

After an epoxidation reaction has been run for a prolonged period of time, the epoxidation catalyst becomes spent.

As used herein, a "spent" epoxidation catalyst refers to an epoxidation catalyst having a cumulative alkylene oxide production of 0.16 kT/m$^3$ of the catalyst or more.

The activity and/or selectivity of an epoxidation catalyst generally decreases with an increase in cumulative alkylene oxide production. In one embodiment, a spent epoxidation catalyst has a cumulative alkylene oxide production of 0.2 kT/m$^3$ of catalyst or more. In one embodiment, a spent epoxidation catalyst has a cumulative alkylene oxide production of 0.3 kT/m$^3$ of catalyst or more. In one embodiment, the spent epoxidation catalyst has a cumulative alkylene oxide production of 0.45 kT/m$^3$ of catalyst or more. In one embodiment, the spent epoxidation catalyst has a cumulative alkylene oxide production of 0.7 kT/m$^3$ of catalyst or more. In one embodiment, the spent epoxidation catalyst has a cumulative alkylene oxide production of 1 kT/m$^3$ of catalyst or more.

In some embodiments, a spent epoxidation catalyst is a catalyst which, when fresh, exhibits an initial activity and an initial selectivity under initial conditions, and the spent epoxidation catalyst exhibits one or more performance decline selected from the group consisting of (a) a 2% or more reduction in selectivity compared to the initial selectivity under the initial conditions, and (b) a 10° C. or more reduction in activity compared to the initial activity under the initial conditions. In this context, prolonged use is not the only reason why the catalyst may become "spent." For example, a "spent" catalyst may have been poisoned or otherwise deactivated. In an advantageous embodiment, the "spent" catalyst has reduced activity and/or selectivity because of a relatively large cumulative alkylene oxide production.

In particular embodiments, the spent catalyst exhibits a 5% or greater reduction in selectivity compared to the initial selectivity under the initial conditions. In another embodiment, the spent catalyst exhibits an 8% or greater reduction in selectivity compared to the initial selectivity under the initial conditions. In another embodiment, the spent catalyst exhibits a 10% or greater reduction in selectivity compared to the initial selectivity under the initial conditions.

Once an epoxidation catalyst becomes spent, the spent epoxidation catalyst may be subjected to the rejuvenation process of the present application. The composition of the epoxidation catalyst is discussed below in more detail.

At a basic level, the rejuvenation process comprises providing a quantity of spent epoxidation catalyst, and depositing an amount of additional silver on the spent epoxidation catalyst to produce the rejuvenated epoxidation catalyst. In one embodiment, the rejuvenation process further comprises depositing one or more rejuvenating promoters on the spent epoxidation catalyst. In one embodiment, the rejuvenation process further comprises depositing one or more rejuvenating copromoters and/or one or more rejuvenating further elements on the spent epoxidation catalyst.

—Optional Wash

Although it is not necessary, it may be desirable to wash the spent epoxidation catalyst before depositing one or more "dopants" on the spent epoxidation catalyst. As used herein, the term "dopant" refers to the additional Group 11 metal, and to any other rejuvenating components deposited on a given substrate.

Washing of the spent epoxidation catalyst generally occurs under conditions effective to remove most of the soluble and/or ionizable materials from the spent epoxidation catalyst and to produce washed spent epoxidation catalyst.

The washing reagent may be, for example water, aqueous solutions comprising additives, such as salts, or an aqueous organic diluent. Suitable salts for inclusion in an aqueous solution include, for example, ammonium salts. Suitable ammonium salts include, for example, ammonium nitrates, ammonium acetates, ammonium carboxylates, ammonium oxalates, ammonium citrates, ammonium fluorides, and combinations thereof. Suitable salts also include other types of nitrates, for example, alkali metal nitrates, such as lithium nitrate. Suitable organic diluents for inclusion in aqueous solution include, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone. In one embodiment, the aqueous liquid is water. In another embodiment, the aqueous liquid is aqueous ammonium nitrate solution.

Where the spent epoxidation catalyst is washed, the wash may take place at any suitable temperature. In one embodiment, the spent epoxidation catalyst is washed at an elevated temperature, for example at a temperature from 30 to 100° C. In one embodiment, the elevated temperature is from 35 to 95° C. The washing may comprise contacting the spent epoxidation catalyst with the aqueous liquid for a period of time. The contact time is not material as long as the contact time is sufficient to remove soluble dopants and/or ionizable materials from the spent epoxidation catalyst. In one embodiment, the contact time may be 24 hours or less. In one embodiment, the contact time may be 10 hours or less. In one embodiment, the contact time is 5 hours or less. In one embodiment, the contact time is 1 hour or more. In one embodiment, the contact time is 0.25 hours or more. In one embodiment, the contact time is 0.05 hours or more.

After the contact time, the liquid comprising materials that have been leached from the spent epoxidation catalyst is removed. The washing may be repeated, for example two or three times, until there is no change in the composition of the effluent. If the spent epoxidation catalyst is washed, then the washed spent epoxidation catalyst may be dried before further treatment by heating at a temperature and for a time sufficient to remove the remaining wash solution.

Drying of the washed spent epoxidation catalyst is not necessary. However, drying typically occurs at a temperature from 100° C. to 300° C. for a period of time. The period of time is not material. In one embodiment, the drying time is 10 hours or less. In one embodiment, the drying time is 5 hours or less. In one embodiment, the drying time is 0.05 hours or more. In one embodiment, the drying time is 0.25 hours or more. In one embodiment, the catalyst is dried at 250° C. for 15 minutes in a catalyst oven in flowing air.

In one embodiment, a quantity of spent epoxidation catalyst pellets is added to an excess of ammonium nitrate solution to form a slurry. Suitable ammonium nitrate solutions have an ammonium nitrate concentration of 0.001% w or more, based on the total weight of the ammonium nitrate solution. Suitable ammonium nitrate solutions have an ammonium nitrate concentration of 85% w or less. In an advantageous embodiment, the ammonium nitrate solution has an ammonium nitrate concentration of 0.03% w.

The resulting slurry is heated at an elevated temperature of from 80° C. to 90° C. In one embodiment, the elevated temperature is maintained for a period of time. A suitable period of time is, for example, 1 hour or more. In one embodiment, the pellets are dried before proceeding. In one embodiment, the pellets are added to a fresh excess of ammonium nitrate solution and heated again at a temperature of from 80° C. to 90° C. The temperature is again maintained for a period of time. Thereafter, the ammonium nitrate solution is decanted and the catalyst pellets are soaked in another excess of ammonium nitrate solution at room temperature (typically from 15° C. to 25° C.). In one embodiment, the room temperature treatment is repeated.

It is not necessary to dry the catalyst before performing the rejuvenation process. In one embodiment, the catalyst is dried, as described previously.

—Rejuvenation Process

The spent epoxidation catalyst typically will already comprise a base amount of one or more Group 11 metals. During the rejuvenation process, additional one or more Group 11 metals are deposited on the spent epoxidation catalyst, producing a total amount of one or more Group 11 metals on the rejuvenated epoxidation catalyst.

The rejuvenation process may be performed inside or outside of an epoxidation reactor. The rejuvenation process comprises contacting the spent epoxidation catalyst with one or more deposition mixtures for depositing one or more dopants under deposition conditions effective to deposit the one or more dopants on the spent epoxidation catalyst. Suitable deposition methods include, for example, impregnation, ion exchange, and the like. Suitable impregnation methods include, for example, vacuum impregnation and pore volume impregnation. In one embodiment, the deposition method is impregnation. In one embodiment, the deposition method is vacuum impregnation.

The rejuvenation process can be a batch or a continuous process.

—Depositing Additional Group 11 Metal

The rejuvenation process comprises depositing additional one or more Group 11 metals or additional one or more cationic Group 11 metal components on the spent epoxidation catalyst. In an advantageous embodiment, the rejuvenation process further comprises depositing one or more rejuvenating promoter components on the spent epoxidation catalyst together with or subsequent to the deposition of the additional Group 11 metal(s) or the additional cationic Group 11 metal component(s), and, if additional cationic Group 11 metal component is deposited, reducing at least a portion of the additional cationic Group 11 metal component(s).

Additional Group 11 metal may be deposited on the spent epoxidation catalyst by contacting the spent epoxidation catalyst with an additional Group 11 metal deposition mixture comprising a liquid containing dispersed Group 11 metal, for example a Group 11 metal sol, and removing the liquid, for example by evaporation, while leaving the additional Group 11 metal on the spent epoxidation catalyst. In an advantageous embodiment, the deposition mixture is a solution of compounds or complexes comprising the additional one or more Group 11 metal.

In an advantageous embodiment, the additional Group 11 metal is silver, and the deposition mixture is a silver deposition mixture. In this embodiment, the silver deposition mixture generally is a solution comprising one or more silver compounds or silver complexes.

Such deposition may be carried out more than once, for example two times or three times, to accomplish the deposition of a desired amount of additional Group 11 metal. The additional Group 11 metal deposition mixture may comprise additives, such as dispersants and stabilizers. Such additives may be removed after the removal of the liquid, by heating for example at a temperature of from 100 to 300° C., in particular from 150 to 250° C., in an inert atmosphere, for example in nitrogen or argon, or in an oxygen containing atmosphere, for example air or a mixture comprising oxygen and argon.

Additional one or more cationic Group 11 metal components may be deposited on the spent epoxidation catalyst using the procedures described above for the one or more additional Group 11 metals. A reducing agent may be applied prior to, together with or after the additional cationic Group 11 deposition mixture.

Typically, the additional cationic Group 11 deposition mixture may comprise the additional cationic Group 11 metal component and a reducing agent, in which case removing the liquid and performing reduction of at least a portion of the additional cationic Group 11 metal component may be accomplished simultaneously. Such deposition may be carried out more than once, for example two times or three times, to accomplish the deposition of a desired amount of additional cationic Group 11 metal. The additional cationic Group 11 metal component includes, for example a non-complexed or complexed Group 11 metal salt, in particular, a cationic Group 11 metal-amine complex.

After the liquid component has been removed, the impregnated spent epoxidation catalyst may be heated at a temperature of from 100 to 900° C., in particular from 150 to 300° C., in an inert atmosphere, for example in nitrogen or argon, or in an oxygen containing atmosphere, for example air or a mixture comprising oxygen and argon. The heating will, in general, effect the reduction of at least a portion of the additional cationic Group 11 metal-amine complex. Examples of cationic Group 11 metal-amine complexes are cationic Group 11 metal complexed with a monoamine or a diamine, in particular a 1,2-alkylene diamine. Examples of suitable amines are ethylene diamine, 1,2-propylene diamine, 2,3-butylene diamine, and ethanol amine. Higher amines may be used, such as, for example, triamines, tetraamines, and pentaamines. Examples of reducing agents are oxalates, lactates and formaldehyde.

For further particulars of cationic Group 11 deposition mixtures comprising cationic Group 11 metal-amine complex and a reducing agent, reference may be made to U.S. Pat. Nos. 5,380,697, 5,739,075, EP-A-266015, and U.S. Pat. No. 6,368,998, which are incorporated herein by reference.

A particularly advantageous additional silver deposition mixture includes, for example, a solution comprising additional cationic silver metal-amine complex. The preparation of an advantageous cationic silver metal-amine complex solution is described in Example 2.

The additional silver deposition mixture is contacted with the spent epoxidation catalyst. The contact time may vary. Suitable contact times include, for example, 1 minute or more. In one embodiment, the contact time is 24 hours or less. The temperature and pressure may vary.

In one embodiment, which may occur in the epoxidation reactor or outside of the epoxidation reactor, the spent epoxidation catalyst is evacuated for a period of time before contacting the spent epoxidation catalyst with one or more deposition mixtures described herein.

In one embodiment, the spent epoxidation catalyst is evacuated to less than 760 mm Hg (atmospheric pressure). In one embodiment, the spent epoxidation catalyst is evacuated to 250 mm Hg or less. In one embodiment, the spent epoxidation catalyst is evacuated to 200 mm Hg or less. In one embodiment, the spent epoxidation catalyst is evacuated to 1 mm Hg or more. In one embodiment, the spent epoxidation catalyst is evacuated to 5 mm Hg or more. In one embodiment, the spent epoxidation catalyst is evacuated to 10 mm Hg or more. Advantageously, the spent epoxidation catalyst is evacuated to 20 mm Hg or more.

In this embodiment, the deposition mixture is contacted with the carrier material after the spent epoxidation catalyst is evacuated. The vacuum may be released before contacting the spent epoxidation catalyst with the deposition mixture. In one embodiment, the vacuum is maintained while the spent epoxidation catalyst is contacted with the deposition mixture. In this embodiment, after contacting the spent epoxidation catalyst with the deposition mixture, the vacuum is released.

The spent epoxidation catalyst may be maintained in contact with the deposition mixture for a contact period sufficient to impregnate the pores in the spent epoxidation catalyst with the deposition mixture, producing an intermediate spent epoxidation catalyst. The specific contact period generally is not material to the impregnation. A typical contact period is 30 seconds or more. As a practical matter, the contact period generally is one minute or more. In one embodiment, the contact period is 3 minutes or more.

The intermediate spent epoxidation catalyst may be separated from excess deposition solution using any known method. For example, excess deposition mixture simply may be decanted or drained from the intermediate spent epoxidation catalyst. For more rapid separation, excess deposition mixture may be removed by mechanical means. Suitable mechanical means include shaking, centrifuging, and the like. The intermediate spent epoxidation catalyst may be allowed to dry or may be exposed to drying conditions.

As an alternative, or in addition, additional Group 11 metal may be deposited on the spent epoxidation catalyst by vapor deposition techniques known in the art.

Where the additional Group 11 metal deposited during the rejuvenation process is silver, the amount of additional silver deposited on the spent epoxidation catalyst generally is 0.2% w or more, based on the total weight of the spent epoxidation catalyst. In one embodiment, the amount of additional silver may be 0.5% w or more, based on the weight of the spent epoxidation catalyst. In one embodiment, the amount of the additional silver may be 1% w or more, based on the weight of the spent epoxidation catalyst. In one embodiment, the amount of the additional silver may be 5% w or more, based on the weight of the spent epoxidation catalyst. In one embodiment, the amount of additional silver may be 8% w or more, based on the weight of the spent epoxidation catalyst. In one embodiment, the amount of additional silver may be 10% w or more, based on the weight of the spent epoxidation catalyst. In one embodiment, the amount of additional silver may be 12% w or more, based on the weight of the spent epoxidation catalyst.

—Depositing Rejuvenating Rhenium

The rejuvenation process also may comprise depositing rhenium. Where rhenium is deposited during the rejuvenation process, the amount of additional rhenium deposited is referred to herein as the "rejuvenating rhenium."

The deposition of rejuvenating rhenium may be effected prior to, together with or subsequent to the deposition of additional Group 11 metal or cationic Group 11 metal component. Rejuvenating rhenium may be deposited using the procedures described above for depositing one or more Group 11 metals.

In particular embodiments, the rejuvenating rhenium deposition mixture may be kept in contact with the spent epoxidation catalyst for a period of time before removing the diluent. The duration of the contact period is not material. In one embodiment, the contact period is 24 hours or less. In one embodiment, the contact period is 5 hours or less. In one embodiment, the contact period is 0.05 hrs or more. In one embodiment, the contact period is 0.25 hours or more.

In an advantageous embodiment, the spent epoxidation catalyst is evacuated as previously described and thereafter contacted with the rejuvenating rhenium mixture. In this embodiment, the contact time may be shortened. The temperature may be up to 95° C., in particular in the range of from 10 to 80° C.

Suitable rejuvenating rhenium mixtures typically comprise the rejuvenating rhenium dissolved or dispersed in an aqueous liquid. Suitable aqueous liquids include, for example, water or an aqueous organic diluent. Suitable aqueous organic diluents include, for example, a mixture of water and one or more of methanol, ethanol, propanol, isopropanol, acetone, or methyl ethyl ketone. The form in which the rejuvenating rhenium may be deposited is not material to the invention. For example, the rejuvenating rhenium may suitably be provided as an oxide or as an oxyanion, for example, as a rhenate or a perrhenate, in salt or acid form. An advantageous solution for depositing rejuvenating rhenium is an ammonium perrhenate solution.

The spent epoxidation catalyst may or may not comprise a base amount of rhenium. The amount of rejuvenating rhenium optionally deposited generally is 0.1 mmole/kg or more of the rejuvenated epoxidation catalyst. In one embodiment, the amount of rejuvenating rhenium is 2 mmole/kg or more of the rejuvenated epoxidation catalyst. In one embodiment, the amount of rejuvenating rhenium is 50 mmole/kg or less of the rejuvenated epoxidation catalyst. In one embodiment, the amount of rejuvenating rhenium is 20 mmole/kg or less of the rejuvenated epoxidation catalyst. Amounts are expressed herein as mmole/kg and μmol/gm. Since 1 mmole/kg=1 μmol/g, the numbers will be the same regardless of whether the content is expressed in terms of μmol/g or mmole/kg.

The deposition may be carried out more than once, for example two times or three times, to accomplish the deposition of a desired amount of rejuvenating rhenium.

—Depositing One or More Rejuvenating Copromoters

The spent epoxidation catalyst may or may not comprise a base amount of one or more copromoters. Where rhenium is already present on the spent epoxidation catalyst and/or where rejuvenating rhenium is deposited on the spent epoxidation catalyst, the rejuvenation process may also comprise depositing an additional amount of one or more rejuvenating rhenium copromoters on the spent epoxidation catalyst.

In particular, when the spent epoxidation catalyst comprises rhenium, the catalyst advantageously may also comprise a rejuvenating rhenium copromoter. Suitable rejuvenating rhenium copromoters may be selected from components comprising an element selected from tungsten, chromium, molybdenum, sulfur, phosphorus, boron, and mixtures thereof. Preferably, the rejuvenating rhenium copromoter is selected from components comprising tungsten, chromium, molybdenum, sulfur, and mixtures thereof. Advantageously, the rejuvenating rhenium copromoter comprises tungsten.

The deposition of rejuvenating copromoter components may be effected prior to, together with or subsequent to the deposition of one or more additional Group 11 metals or additional cationic Group 11 metal components and/or optional rejuvenating promoter components using the deposition procedures and liquids described above with respect to rhenium.

The form in which the rejuvenating copromoter component may be deposited is not material to the invention. For example, the rejuvenating copromoter component suitably may be provided as an oxide or as an oxyanion, in salt or acid form. For example, the rejuvenating copromoter component may be provided as a tungstate, a chromate, a molybdate, a sulfate, or a combination thereof. An advantageous rejuvenating copromoter deposition mixture for depositing tungsten comprises an ammonium tungstate solution.

When deposited, a suitable quantity of the rejuvenating copromoter is 0.01 mmole/kg or more, based on the weight of the rejuvenated catalyst, calculated on the basis of pore impregnation of the spent epoxidation catalyst. In one embodiment, the amount of each rejuvenating copromoter is 0.1 mmole/kg or more on the same basis. In one embodiment, the amount of each rejuvenating copromoter is 40 mmole/kg or less on the same basis. In one embodiment, the amount of each rejuvenating copromoter is 20 mmole/kg or less on the same basis.

—Depositing One or More Rejuvenating Further Elements

The rejuvenation process may also comprise depositing one or more components comprising one or more rejuvenating further elements on the spent epoxidation catalyst. The spent epoxidation catalyst may or may not comprise a base amount of the one or more further elements.

Eligible rejuvenating further elements may be selected from the group of nitrogen, fluorine, alkali metals, alkaline earth metals, titanium, hafnium, zirconium, vanadium, thallium, thorium, tantalum, niobium, gallium, germanium, and mixtures thereof. Preferred rejuvenating alkali metals are selected from sodium, lithium, potassium, rubidium, cesium, and mixtures thereof. Most preferred rejuvenating alkali metals are selected from lithium, potassium, cesium, and mixtures thereof. Preferred rejuvenating alkaline earth metals are selected from calcium, magnesium, barium, and mixtures thereof.

The rejuvenating further elements optionally may be deposited in any form. For example, salts of rejuvenating alkali metals and/or rejuvenating alkaline earth metals are suitable. Suitable liquid rejuvenating further element deposition mixtures comprise the component(s) comprising one or more rejuvenating further elements dissolved or dispersed in an aqueous liquid, for example water or an aqueous organic diluent, such as for example a mixture of water and one or more of methanol, ethanol, propanol, isopropanol, tetrahydrofuran, ethylene glycol, ethylene glycol dimethyl ether, diethylene glycol dimethyl ether, dimethylformamide, acetone or methyl ethyl ketone. The deposition may be carried out more than once, for example two times or three times, to accomplish the deposition of a desired amount of the component(s) comprising the rejuvenating further elements. Alternatively, different components comprising one or more different rejuvenating further elements may be deposited in different deposition steps.

In an advantageous embodiment, the rejuvenating further element deposition mixture for depositing rejuvenating alkali metals and/or rejuvenating alkaline earth metals are metal hydroxide solutions.

The deposition of components comprising the rejuvenating further elements may be effected prior to, together with or subsequent to the deposition of additional Group 11 metal or additional cationic Group 11 metal component; prior to, together with or subsequent to the optional deposition of rejuvenating rhenium; and, prior to, together with or subsequent to the optional deposition of the rejuvenating copromoter components. The procedures described above also apply to the deposition of the one or more rejuvenating further elements.

The quantities of various rejuvenating further elements that may be deposited on the spent epoxidation catalyst are described below. As used herein, unless otherwise specified, the quantity of alkali metal present in an epoxidation catalyst is deemed to be the quantity insofar as it can be extracted from the epoxidation catalyst. The extraction generally involves microwaving 0.5 g of catalyst in 25 g of 0.1 wt. % solution of sodium chloride and determining in the extract the relevant metals by using a known method, for example atomic absorption spectroscopy.

As used herein, unless otherwise specified, the quantity of alkaline earth metal present in an epoxidation catalyst is deemed to be the quantity insofar as it can be extracted from the epoxidation catalyst with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. For examples of such methods, reference is made to U.S. Pat. No. 5,801,259, which is incorporated herein by reference.

With the exception of lithium, the amount of rejuvenating further elements may be 0.1 mmole/kg or more of the rejuvenated epoxidation catalyst. In one embodiment, the amount of rejuvenating further elements is 50 mmole/kg or less of the rejuvenated epoxidation catalyst.

When the rejuvenating further element comprises one or more alkali metal, the total amount of rejuvenating alkali metal with the exception of lithium generally is 0.1 mmole/kg or more of the rejuvenated epoxidation catalyst. In one embodiment, the total amount of rejuvenating alkali metal other than lithium on the rejuvenated epoxidation catalyst is 0.2 mmole/kg or more of the rejuvenated epoxidation catalyst. In one embodiment, the total amount of rejuvenating alkali metal other than lithium on the rejuvenated epoxidation catalyst is 50 mmole/kg or less of the rejuvenated epoxidation catalyst. In one embodiment, the total amount of rejuvenating alkali metal other than lithium on the rejuvenated epoxidation catalyst is 30 mmole/kg or less of the rejuvenated epoxidation catalyst.

Where lithium is used as a rejuvenating alkali metal, the total amount of rejuvenating lithium is 1 mmole/kg or more of the rejuvenated epoxidation catalyst. In one embodiment, the total amount of rejuvenating lithium is 100 mmole/kg or less of the rejuvenated epoxidation catalyst. Where rejuvenating cesium is deposited, the amount of rejuvenating cesium is 0.1 mmole/kg or more of the rejuvenated epoxidation catalyst. In one embodiment, the amount of rejuvenating cesium is 0.2 mmole/kg or more of the rejuvenated epoxidation catalyst. In one embodiment, the amount of rejuvenating cesium is 1 mmole/kg or more of the rejuvenated epoxidation catalyst. In one embodiment, the amount of rejuvenating cesium is 50 mmole/kg or less of the rejuvenated epoxidation catalyst. In one embodiment, the amount of rejuvenating cesium is 30 mmole/kg or less of the rejuvenated epoxidation catalyst. In one embodiment, the amount of rejuvenating cesium is 10 mmole/kg or less of the rejuvenated epoxidation catalyst.

Where rejuvenating alkaline earth metal is added, an advantageous amount of rejuvenating alkaline earth metal is 1 mmole/kg or more of the rejuvenated epoxidation catalyst. In one embodiment, the amount of rejuvenating alkaline earth metal is 100 mmole/kg or less of the rejuvenated epoxidation catalyst.

Methods for depositing Group 11 metal, rhenium, copromoter components, and one or more component comprising a further element on a carrier material are known in the art and such methods may be applied in the practice of the rejuvenation process. For examples of such methods, reference may be made to U.S. Pat. Nos. 5,380,697, 5,739,075, EP-A-266015, and U.S. Pat. No. 6,368,998, which are incorporated herein by reference. Suitably, such methods include impregnating the particulate carrier materials with a liquid mixture comprising cationic Group 11 metal-amine complex and a reducing agent.

In one embodiment, additional silver, rejuvenating lithium, and rejuvenating cesium are deposited on the spent epoxidation catalyst. In this embodiment, the amount of additional silver advantageously is 12% w or more of the rejuvenated epoxidation catalyst. In this embodiment, the amount of rejuvenating cesium produces 300 ppmw or more extracted cesium. In one embodiment, the amount of rejuvenating cesium produces 370 ppmw or more extracted cesium. In one embodiment, the amount of rejuvenating cesium produces 600 ppmw or less extracted cesium. In one embodiment, the amount of rejuvenating cesium produces 520 ppmw or less extracted cesium. In this embodiment, the amount of rejuvenating lithium is 40 µmole/g of the rejuvenated epoxidation catalyst.

In another advantageous embodiment, the rejuvenation process deposits additional silver onto the spent epoxidation catalyst along with a combination of components comprising rhenium, tungsten, cesium, and lithium. In one embodiment, one or more dopants are deposited on the spent epoxidation catalyst by contacting the spent epoxidation catalyst under deposition conditions with a cationic silver metal-amine complex solution and deposition mixtures selected from the group consisting of ammonium perrhenate solutions, ammonium tungstate solutions, lithium hydroxide solutions, cesium hydroxide solutions, and combinations thereof.

In one embodiment, an advantageous amount of additional silver is 8% w or more, based on the weight of the spent epoxidation catalyst. An advantageous amount of rejuvenating cesium produces from 300 ppm to 1000 ppm extracted cesium. An advantageous amount of rejuvenating rhenium is from 1 mmole/kg to 5 mmole/kg of the rejuvenated epoxidation catalyst, calculated by pore volume impregnation of the spent epoxidation catalyst. An advantageous amount of rejuvenating tungsten is from 0.5 mmole/kg to 5 mmole/kg of the rejuvenated epoxidation catalyst, calculated by pore volume impregnation of the spent epoxidation catalyst. An advantageous amount of rejuvenating lithium is from 10 mmole/kg to 40 mmole/kg of the rejuvenated epoxidation catalyst, calculated by pore volume impregnation of the spent epoxidation catalyst.

In an advantageous embodiment: the amount of additional silver is 8% w or more, based on the weight of the spent epoxidation catalyst; the amount of rejuvenating cesium produces from 600 ppm to 650 ppm extracted cesium; and, the amount of the following materials are as indicated, based on the weight of the rejuvenated epoxidation catalyst, calculated by pore volume impregnation of the spent epoxidation catalyst: rejuvenating rhenium, 2 mmole/kg or more; rejuvenating tungsten, 0.6 mmole/kg or more; rejuvenating lithium, 15 mmole/g.

The deposition conditions may be generated inside or outside of the epoxidation reactor. In one embodiment, the deposition conditions are generated in the epoxidation reactor.

—The Rejuvenated Epoxidation Catalyst Exhibits Increased Selectivity, Increased Activity, or a Combination of Both The rejuvenation process produces rejuvenated epoxidation catalyst which exhibits increased selectivity, increased activity, or a combination thereof. As used herein, the selectivity is the quantity of olefin oxide formed, relative to the quantity of olefin converted, expressed in mole-%.

Advantageously, the rejuvenated epoxidation catalyst exhibits an increase in selectivity of 1-mole % or more, compared to selectivity of the spent epoxidation catalyst. In one embodiment, the rejuvenated epoxidation catalyst exhibits an increase in selectivity of 5 mole-% or more, compared to selectivity of the spent epoxidation catalyst. In one embodiment, the rejuvenated epoxidation catalyst exhibits an increase in selectivity of 7 mole-% or more, compared to selectivity of the spent epoxidation catalyst. More advantageously, the rejuvenated epoxidation catalyst exhibits an increase in selectivity of 10 mole-% or more, compared to selectivity of the spent epoxidation catalyst. Even more advantageously, the rejuvenated epoxidation catalyst exhibits an increase in selectivity of 12 mole-% or more, compared to selectivity of the spent epoxidation catalyst.

In one embodiment, the present application provides a process for rejuvenating spent epoxidation catalyst which increases activity of the spent epoxidation catalyst. Increased activity of the rejuvenated epoxidation catalyst is evidenced by a reduction in the temperature required to produce a given amount of alkylene oxide (the "production temperature"), compared to the production temperature of the spent epoxidation catalyst. A 5° C. reduction in the production temperature is the same as a 5° C. increase in activity.

In one embodiment, the production temperature of the rejuvenated epoxidation catalyst is reduced by 2° C. or more compared to the production temperature of the spent epoxidation catalyst. In one embodiment, the production temperature of the rejuvenated epoxidation catalyst is reduced by 3° C. or more compared to the production temperature of the spent epoxidation catalyst. In one embodiment, the production temperature of the rejuvenated epoxidation catalyst is reduced by 4° C. or more compared to the production temperature of the spent epoxidation catalyst. In one embodiment, the production temperature of the rejuvenated epoxidation catalyst is reduced by 5° C. or more compared to the production temperature of the spent epoxidation catalyst. In one embodiment, the production temperature is reduced by 8° C. or more compared to the production temperature of the spent epoxidation catalyst. In one embodiment, the production temperature is reduced by 9° C. or more compared to the production temperature of the spent epoxidation catalyst.

In one embodiment, the production temperature of the rejuvenated epoxidation catalyst is reduced by 40° C. or less compared to the production temperature of the spent epoxidation catalyst. In one embodiment, the production temperature of the rejuvenated epoxidation catalyst is reduced by 20° C. or less compared to the production temperature of the spent epoxidation catalyst. In one embodiment, the production temperature of the rejuvenated epoxidation catalyst is reduced by 15° C. or less compared to the production temperature of the spent epoxidation catalyst. In one embodiment, the production temperature of the rejuvenated epoxidation catalyst is reduced by 12° C. or less compared to the production temperature of the spent epoxidation catalyst. In one embodiment, the production temperature of the rejuvenated epoxidation catalyst is reduced by 10° C. or less compared to the production temperature of the spent epoxidation catalyst.

The rejuvenation process may be performed successive times after the epoxidation catalyst has been used again following an earlier rejuvenation. After completing the rejuvenation process, a feed comprising the olefin and oxygen may be reacted in the presence of the rejuvenated epoxidation catalyst using any suitable method.

The Spent Epoxidation Catalyst

The rejuvenation process may be used to rejuvenate a variety of spent epoxidation catalysts. Typically, the epoxidation catalyst is solid under the conditions of the epoxidation reaction. In one embodiment, the catalysts may form a packed bed in the epoxidation reactor.

In one embodiment, the epoxidation catalyst comprises one or more Group 11 metals. In one embodiment, the Group 11 metals may be selected from the group consisting of silver and gold. Preferably, the Group 11 metal comprises silver. In particular, the Group 11 metal comprises silver in a quantity of at least 90% w, more in particular at least 95% w, for example at least 99% w, or at least 99.5% w, calculated as the weight of silver metal relative to the total weight of the Group 11 metal, as metal. The epoxidation catalyst exhibits appreciable catalytic activity when the Group 11 metal content is at least 10 g/kg, relative to the weight of the catalyst, as measured by nitric acid digestion and silver titration. Preferably, the catalyst comprises the Group 11 metal in a quantity of from 50 to 500 g/kg, more preferably from 100 to 400 g/kg, based on the total weight of the epoxidation catalyst. As discussed above, in an advantageous embodiment, the Group 11 metal is silver.

The epoxidation catalyst optionally may comprise rhenium. In some embodiments, the epoxidation catalyst may comprise a carrier material on which the Group 11 metal, optional rhenium, and any optional components comprising one or more copromoter and/or one or more further elements may be deposited. Rhenium, suitable copromoter components, and suitable components comprising one or more further elements are hereinbefore described. Suitable carrier materials are described below.

Where the epoxidation catalyst comprises rhenium, the amount of rhenium present on the epoxidation catalyst typically ranges from 0.1 mmoles to 10 mmoles per kilogram of total catalyst. In one embodiment, the epoxidation catalyst comprises from 0.2 mmoles to 5 mmoles per kilogram of total catalyst. Stated another way, the epoxidation catalyst may comprise from 19 to 1860 parts by weight of rhenium per million parts by weight of total catalyst ("ppmw"). In one embodiment, the epoxidation catalyst may comprise from 37 to 930 ppmw.

Eligible further elements are described hereinbefore. With the exception of lithium, the amount of further elements present on the spent epoxidation catalyst may be about 1 mmole/kg or more, based on the total weight of the spent epoxidation catalyst. In one embodiment, the amount of further elements is about 50 mmol/kg or less on the same basis. Where lithium is present on the spent epoxidation catalyst, the total amount of lithium generally is about 1 mmole/kg or more on the same basis. In one embodiment, the total amount of lithium is about 100 mmole/kg or less on the same basis. The further elements may be provided in any form. For example, salts of an alkali metal or an alkaline earth metal are suitable.

The dopants may be deposited on a carrier material using methods known in the art. See, for example, U.S. Pat. Nos. 5,380,697, 5,739,075, EP-A-266015, and U.S. Pat. No. 6,368,998, which are incorporated herein by reference. Suitably, the methods include impregnating the particulate carrier materials with a liquid mixture comprising cationic Group 11 metal-amine complex and a reducing agent.

—The Carrier Material

The epoxidation catalyst comprises a carrier material. The carrier material may be natural or artificial inorganic material, and may include refractory materials, silicon carbide, clays, zeolites, charcoal and alkaline earth metal carbonates, for example calcium carbonate. In an advantageous embodiment, the carrier material comprises one or more refractory materials. Examples of suitable refractory materials include, for example, alumina, magnesia, zirconia and silica. In an advantageous embodiment, the carrier material is α-alumina. In this embodiment, the carrier material typically comprises at least 85% w, more typically at least 90% w, in particular at least 95% w α-alumina, frequently up to 99.9% w α-alumina, relative to the weight of the carrier. Other components of the α-alumina may comprise, for example, silica, alkali metal components, for example sodium and/or potassium components, and/or alkaline earth metal components, for example calcium and/or magnesium components.

The surface area of the carrier material may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 10 m$^2$/g, preferably at most 5 m$^2$/g, and in particular at most 3 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carrier materials, in particular when they are an α-alumina optionally comprising in addition silica, alkali metal and/or alkaline earth metal components, provide improved performance and stability of operation.

The water absorption of the carrier material is typically in the range of from 0.2 to 0.8 g/g, preferably in the range of from 0.3 to 0.7 g/g. A higher water absorption may be in favor in view of a more efficient deposition of one or more dopants. As used herein, water absorption is as measured in accordance with ASTM C20, and water absorption is expressed as the weight of the water that can be absorbed into the pores of the carrier, relative to the weight of the carrier.

The particulate carrier material may have a pore size distribution such that pores with diameters in the range of from 0.2 to 10 μm represent at least 70% of the total pore volume. Such relatively narrow pore size distribution can contribute to one or more of the activity, selectivity and longevity of the catalyst. Longevity may be in respect of maintaining the catalyst activity and/or maintaining the selectivity. As used herein, the pore size distribution and the pore volumes are as measured by mercury intrusion to a pressure of 3.0×10$^8$ Pa using a Micrometrics Autopore 9200 model (130° contact angle, mercury with a surface tension of 0.473 N/m, and correction for mercury compression applied).

In an advantageous embodiment, the pore size distribution is such that the pores with diameters in the range of from 0.2 to 10 μm represent more than 75%, in particular more than 80%, more preferably more than 85%, most preferably more than 90% of the total pore volume. Frequently, the pore size distribution is such that the pores with diameters in the range of from 0.2 to 10 μm represent less than 99.9%, more frequently less than 99% of the total pore volume.

In an advantageous embodiment, the pore size distribution is such that the pores with diameters in the range of from 0.3 to 10 μm represent more than 75%, in particular more than 80%, more preferably more than 85%, most preferably more than 90%, in particular up to 100%, of the pore volume contained in the pores with diameters in the range of from 0.2 to 10 μm.

Typically, the pore size distribution is such that pores with diameters of less than 0.2 μm represent less than 10%, in particular less than 5%, of the total pore volume. Frequently, the pores with diameters less than 0.2 μm represent more than 0.1%, more frequently more than 0.5% of the total pore volume.

Typically, the pore size distribution is such that pores with diameters greater than 10 μm represent less than 20%, in particular less than 10%, more in particular less than 5%, of the total pore volume. Frequently, the pores with diameters greater than 10 μm represent more than 0.1%, in particular more than 0.5% of the total pore volume.

Typically, the pores with diameters in the range of from 0.2 to 10 μm provide a pore volume of at least 0.25 ml/g, in particular at least 0.3 ml/g, more in particular at least 0.35 ml/g. Typically, the pores with diameters in the range of from 0.2 to 10 μm provide a pore volume of at most 0.8 ml/g, more typically at most 0.7 ml/g, in particular at most 0.6 ml/g.

The Epoxidation Process

The rejuvenated epoxidation catalyst may be used to catalyze an epoxidation process. The epoxidation process may be carried out in many ways. In one embodiment, the epoxidation process is a gas phase process, i.e., a process in which the feed is contacted in the gas phase with the epoxidation catalyst which is present as a solid material, typically in a packed bed. Generally the epoxidation process is a continuous process.

The olefin for use in the epoxidation process may be any olefin. Suitable olefins include aromatic olefins, for example styrene, or di-olefins, whether conjugated or not, for example 1,9-decadiene or 1,3-butadiene. Typically, the olefin is a monoolefin, for example 2-butene or isobutene. In one embodiment, the olefin is a mono-α-olefin, for example 1-butene or propylene. In an advantageous embodiment, the olefin is ethylene.

The olefin concentration in the feed to the epoxidation process may be selected within a wide range. Typically, the olefin concentration in the feed will be 80 mole % or less, relative to the total feed. In one embodiment, the olefin concentration will be from 0.5 to 70 mole %, relative to the total feed. In one embodiment, the olefin concentration will be from 1 to 60 mole %, relative to the total feed. As used herein, the feed is considered to be the composition which is contacted with the epoxidation catalyst.

The epoxidation process may be air-based or oxygen-based, see "Kirk-Othmer Encyclopedia of Chemical Technology", $3^{rd}$ edition, Volume 9, 1980, pp. 445-447. In an air-based process, air or air enriched with oxygen is employed as the source of the oxidizing agent while in an oxygen-based processes, high-purity (95 mole % or more) oxygen is employed as the source of the oxidizing agent.

The oxygen concentration in the feed may be selected within a wide range. However, in practice, oxygen is generally applied at a concentration which avoids the flammable regime. Typically, the concentration of oxygen applied will be from 1 to 15 mole %, more typically from 2 to 12 mole % of the total feed.

In order to remain outside the flammable regime, the concentration of oxygen in the feed may be lowered as the concentration of the olefin is increased. The actual safe operating ranges depend on the feed composition, and also on the reaction conditions such as the reaction temperature and the reaction pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, organic nitrates, hydrazine, hydroxylamine, ammonia, or combinations thereof may be employed as well. Without limiting the application to a theory, it is frequently considered that under the operating conditions of olefin epoxidation the nitrogen containing reaction modifiers are precursors of nitrates or nitrites, i.e., they are so-called nitrate- or nitrite-forming compounds (cf. e.g. EP-A-3642 and U.S. Pat. No. 4,822,900, which are incorporated herein by reference).

In an advantageous embodiment, the reaction modifiers are organic halides. Suitable organic halides include, for example, organic bromides and organic chlorides. In an advantageous embodiment, the organic halides are chlorohydrocarbons or bromohydrocarbons. In a particularly advantageous embodiment, the reaction modifiers are selected from the group of methyl chloride, ethyl chloride, ethylene dichloride, ethylene dibromide, vinyl chloride, and mixtures thereof. In a particularly advantageous embodiment, the reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates, and nitrites. Examples include nitromethane, 1-nitropropane or 2-nitropropane. In an advantageous embodiment, nitrate- or nitrite-forming compounds, e.g. nitrogen oxides and/or organic nitrogen compounds, are used together with an organic halide, in particular an organic chloride.

The reaction modifiers generally are effective when used at a concentration in the feed of, for example up to 0.1 mole %, relative to the total feed, for example from $0.01 \times 10^{-4}$ to 0.01 mole %. In an advantageous embodiment, where the olefin is ethylene, the reaction modifier is present in the feed at a concentration of from $0.1 \times 10^{-4}$ to $50 \times 10^{-4}$ mole %. In another advantageous embodiment, the reaction modifier is present in the feed at a concentration of from $0.3 \times 10^{-4}$ to $30 \times 10^{-4}$ mole %, relative to the total feed.

In addition to the olefin, oxygen, and the reaction modifier, the feed may contain one or more optional components, such as one or more of carbon dioxide, inert gases, and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole %, relative to the total feed, is avoided. In an advantageous embodiment, a concentration of carbon dioxide in the feed in excess of 10 mole %, relative to the total feed, is avoided. A concentration of carbon dioxide as low as 1 mole % or lower, relative to the total feed, may be employed.

Inert gases, for example nitrogen or argon, may be present in the feed in a concentration of from 30 to 90 mole %, typically from 40 to 80 mole %.

Suitable saturated hydrocarbons which may be present in the feed include, for example, methane and ethane. If saturated hydrocarbons are present, they may be present in a quantity of 80 mole % or less, relative to the total feed. In an advantageous embodiment, saturated hydrocarbons are present in a quantity of 75 mole % or less, relative to the total feed. Frequently, saturated hydrocarbons are present in a quantity of 30 mole % or more, more frequently 40 mole % or more, relative to the total feed. Saturated hydrocarbons may be added to the feed in order to increase the oxygen flammability limit.

The epoxidation process may be carried out using reaction temperatures selected from a wide range. Advantageous reaction temperatures are in the range of from 150 to 325° C. In a particularly advantageous embodiment, the reaction temperatures are in the range of from 180 to 300° C.

Advantageously, the epoxidation process is carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Advantageously, when the epoxidation process is as a gas phase process involving a packed catalyst bed, the GHSV is in the range of from 1500 to 10000 Nl/(l.h). Advantageously, the process is carried out at a work rate of from 0.5 to 10 kmole olefin oxide produced per $m^3$ of catalyst per hour. In one embodiment, the process is carried out at a work rate of from 0.7 to 8 kmole olefin oxide produced per $m^3$ of catalyst per hour. In one embodiment, the process is carried out at a work rate of, for example, 5 kmole olefin oxide produced per m³ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

—Conversion of Olefin Oxide into a 1,2-Diol, a 1,2-Diol Ether, or an Alkanolamine The olefin oxide produced in the epoxidation process may be converted by conventional methods into a 1,2-diol, a 1,2-diol ether, a 1,2-carbonate or an alkanol amine.

The conversion into the 1,2-diol or the 1,2-diol ether may comprise, for example, reacting the ethylene oxide with water, in a thermal process or by using a catalyst, which may be an acidic catalyst or a basic catalyst. For example, for making predominantly the 1,2-diol and less 1,2-diol ether, the olefin oxide may be reacted with a ten fold molar excess of water, in a liquid phase reaction in the presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting it with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The 1,2-diols and 1,2 diol ethers, for example ethylene glycol, 1,2-propylene glycol and ethylene glycol ethers may be used in a large variety of industrial applications, for example in the fields of food, beverages, tobacco, cosmetics, thermoplastic polymers, curable resin systems, detergents, heat transfer systems, etc. The 1,2-carbonates, for example ethylene carbonate, may be used as a diluent, in particular as a solvent. Ethanol amines may be used, for example, in the treating ("sweetening") of natural gas.

The conversion into the alkanolamine may comprise, for example, reacting the olefin oxide with ammonia. Anhydrous or aqueous ammonia may be used, although anhydrous ammonia is typically used to favour the production of monoalkanolamine. For methods applicable in the conversion of the olefin oxide into the alkanolamine, reference may be made, for example, to U.S. Pat. No. 4,845,296, which is incorporated herein by reference.

Unless specified otherwise, the organic compounds mentioned herein, for example the olefins, alcohols, 1,2-diols, 1,2-diol ethers, 1,2-carbonates, alkanol amines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) or for other parameters include the numbers specified for the limits of the ranges.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

—Suitable Reactors

The process of rejuvenating an epoxidation catalyst may be applicable with the epoxidation catalyst present in any reactor suitable for the epoxidation of an olefin. Suitable reactors include, for example, one or more microchannel reactors, shell-and-tube heat exchanger reactors, stirred tank reactors, bubble columns or condensation apparatus. The present invention encompasses the use of such reactors or condensation apparatus, or the use of a plurality of reactors or condensation apparatus in these processes.

Advantageous reactors include, for example, reactors in the form of shell-and-tube heat exchangers and microchannel reactors. It is an advantageous aspect of the invention that during the rejuvenation process, the epoxidation catalyst may be present in the epoxidation reactor. In an advantageous embodiment, the rejuvenation process is performed in the reaction tubes of a shell-and-tube heat exchanger reactor. This aspect eliminates the need for removing the epoxidation catalyst from the epoxidation reactor, and the catalyst may stay in place after the rejuvenation for use during a further period of production of the olefin oxide from the olefin and oxygen.

The following examples are intended to illustrate the advantages of the present invention and are not intended to unduly limit the scope of the invention.

EXAMPLE 1

Washing of Spent Catalyst

In the following examples, the following procedure was used to wash the spent catalysts to produce washed spent catalyst, which was used in the various attempts to rejuvenate the respective spent catalyst.

140 g of the spent catalyst was added to 202 grams of 0.03 w % ammonium nitrate solution. The temperature was brought up to 85° C. and held at 85±5° C. for 1 hour. The pellets were decanted and dried at 250° C. in flowing air for 15 minutes. The catalyst pellets were added to a fresh portion of 200 grams of 0.03 w % ammonium nitrate and heated for 1 hour at 87.5° C. (±5° C.). The ammonium nitrate solution was decanted and the catalyst pellets were soaked in 200 g of 0.03 w % ammonium nitrate solution at room temperature. The room temperature treatment was repeated one more time. Finally the spent catalyst was dried for 15 minutes at 250° C. This procedure removed most of the soluble dopants from the respective spent catalyst and produced a washed spent catalyst.

EXAMPLE 2

Preparation of Stock Silver Solution

This Example describes the preparation of a stock silver impregnation solution used for impregnating various support materials as described in the following Examples.

In a 5-liter stainless steel beaker, 415 grams of reagent grade sodium hydroxide was dissolved in 2340 ml of deionized water. The temperature of the solution was adjusted to 50° C. In a 4-liter stainless steel beaker 1699 grams of silver nitrate was dissolved in 2100 ml of deionized water. The temperature of the solution was adjusted to 50° C. The sodium hydroxide solution was slowly added to the silver nitrate solution with stirring while the temperature was maintained at 50° C. The resulting slurry was stirred for 15 minutes. The pH of the solution was maintained at above 10 by the addition of NaOH solution as required. A liquid removal procedure was used which included removing liquid by the use of a filter wand followed by the replacement of the removed liquid with an equivalent volume of deionized water. This liquid removal procedure was repeated until the conductivity of the filtrate dropped below 90 micro-mho/cm. After the completion of the last liquid removal cycle, 1500 ml of deionized water was added and followed by the addition of 630 grams of oxalic acid dihydrate (4.997 moles) in increments of 100 grams while stirring and maintaining the solution at 40° C. (±5° C.). The pH of the solution was monitored during the addition of the last 130 grams of oxalic acid dihydrate to ensure that the pH did not drop below 7.8 for an extended period of time. Water was removed from the solution with a filter wand and the slurry was cooled to less than 30° C. Slowly added to the solution was 732 grams of 92 w % ethylenediamine (EDA). The temperature was maintained below 30° C. during this addition. A spatula was used to manually mix the mixture until enough liquid was present to mechanically stir the mixture.

EXAMPLE 3

Comparative Example

In this comparative example, an attempt was made to rejuvenate a spent epoxidation catalyst (the "comparative catalyst") comprising an α-alumina carrier doped with silver, rhenium, cesium, and tungsten. The spent epoxidation catalyst had a cumulative alkylene oxide production of 2.4 kT/m$^3$ of catalyst. The silver content of the spent comparative catalyst was 23% w, based on the total weight of the spent comparative catalyst. The silver content was determined by nitric acid digestion and silver titration.

Pellets of the spent comparative catalyst were washed using the procedure described in Example 1 to produce washed spent comparative catalyst. An additivated spent comparative catalyst was prepared by depositing the following on the washed spent comparative catalyst: rhenium; tungsten; lithium; and cesium. The deposition solution for preparing the additivated comparative catalyst contained no silver.

The deposition solution was prepared by dissolving: 0.1731 grams of NH$_4$ReO$_4$ in 2 g of 1:1 EDA/H$_2$O; 0.0483 g of ammonium metatungstate in 2 g of 1:1 ammonia/water; and 0.2030 g LiOHxH$_2$O in water. Additional water was added to a mixture of the foregoing solutions to adjust the solution weight to 100 grams. The resulting solution was mixed with 0.4639 g of 50 w % CsOH solution. This combined deposition mixture was used to prepare the additivated comparative catalyst.

30 grams of the washed comparative catalyst pellets were evacuated to 20 mm Hg for 1 minute and the combined deposition mixture was added to the washed comparative catalyst pellets while under vacuum. The vacuum was released and the resulting evacuated comparative catalyst pellets were allowed to contact the combined deposition mixture for 3 minutes, producing intermediate comparative catalyst pellets. The intermediate comparative catalyst pellets were centrifuged at 500 rpm for 2 minutes to remove excess liquid, producing centrifuged intermediate comparative catalyst pellets. The centrifuged intermediate comparative catalyst pellets were placed in a vibrating shaker and dried in flowing air at 250° C. for 5½ minutes, producing additivated comparative catalyst pellets.

The silver content was 23 w % Ag and the cesium content was 650 ppm Cs/g, based on the total weight of the additivated comparative catalyst pellets. The silver and extracted cesium content of the additivated comparative catalyst pellets were determined as described above. The additivated comparative catalyst pellets also comprised the following, calculated on the basis of pore volume impregnation: 2.0 µmole Re/g additivated comparative catalyst; 0.60 µmole W/g additivated comparative catalyst; and, 15 µmole LiOH/g additivated comparative catalyst.

Preparation of Rejuvenated Catalysts

EXAMPLE 4

In Examples 4 and 5, pellets of two spent epoxidation catalysts were subjected to a rejuvenation process which included the deposition of additional silver. One of the catalysts (Catalyst A) comprised α-alumina doped with silver, lithium, and cesium. The other catalyst (Catalyst B) comprised α-alumina doped with silver, rhenium, tungsten, cesium, and lithium. The spent epoxidation catalysts had a cumulative alkylene oxide production of 0.16 kT/m$^3$ of catalyst or more.

The silver content of spent catalysts A and B was determined. The cesium content of spent catalysts A and B was determined both before and after washing using the procedures described in Example 1. The results are given in the following Table:

|  | Dopants present on spent catalyst | Ag w % | Cs, ppm before washing | Cs, ppm after washing |
|---|---|---|---|---|
| Spent Catalyst A | Ag, Cs, Li | 14.5 | 326 | 72 |
| Spent Catalyst B | Ag, Cs, Li, Re, W | 13.65 | 394 | 45 |

A combined deposition solution for preparing rejuvenated catalyst A was made by mixing: 153 grams of silver stock solution of specific gravity 1.553 g/cc; a solution of 0.1978 g of NH$_4$ReO$_4$ in 2 g of 1:1 EDA/H$_2$O; 0.0552 g of ammonium metatungstate dissolved in 2 g of 1:1 ammonia/water; and, 0.231 g LiOHxH$_2$O dissolved in water. Additional water was added to adjust the specific gravity of the solution to 1.454 g/cc. 50 grams of the resulting solution was mixed with 0.1616 g of 50 w % CsOH solution, producing the combined deposition mixture. The combined deposition mixture was used to prepare rejuvenated catalyst A.

30 grams of pellets of washed spent catalyst A were evacuated to 20 mm Hg for 1 minute and the combined deposition mixture was added to the pellets of washed spent catalyst A while under vacuum. The vacuum was then released and the resulting evacuated pellets of spent catalyst A were allowed to contact the combined deposition mixture for 3 minutes, producing an intermediate catalyst A. The pellets of intermediate catalyst A were then centrifuged at 500 rpm for 2 minutes to remove excess liquid. The resulting centrifuged pellets of intermediate catalyst A were placed in a vibrating shaker and dried in flowing air at 250° C. for 5½ minutes, producing rejuvenated catalyst A.

The final composition of the rejuvenated catalyst A pellets was determined. The rejuvenated catalyst A pellets comprised 23.5 w % Ag, based on the total weight of rejuvenated catalyst A and 639 ppm of extracted Cs/g of rejuvenated catalyst. The silver and extracted cesium content of the rejuvenated catalyst A pellets were determined as described above. The rejuvenated catalyst A pellets also comprised the following, calculated on the basis of pore volume impregnation: 2.0 µmole Re/g of rejuvenated catalyst A; 0.60 µmole W/g of rejuvenated catalyst A; and, 15 µmole LiOH/g of rejuvenated catalyst A.

EXAMPLE 5

The deposition mixture for preparing rejuvenated catalyst B was made by mixing: 153 grams of silver stock solution of specific gravity 1.553 g/cc; a solution of 0.2037 g of $NH_4ReO_4$ in 2 g of 1:1 $EDA/H_2O$; 0.0568 g of ammonium metatungstate dissolved in 2 g of 1:1 ammonia/water; and, 0.2390 g $LiOHxH_2O$ dissolved in water. Additional water was added to adjust the specific gravity of the solution to 1.451 g/cc. 50 grams of such solution was mixed with 0.1803 g of 50 w % CsOH solution, producing the combined deposition mixture. This combined deposition mixture was used to prepare rejuvenated catalyst B.

30 grams of washed spent catalyst B pellets were evacuated to 20 mm Hg for 1 minute and the combined deposition mixture was added to the washed spent catalyst B pellets while under vacuum. The vacuum was released and the resulting evacuated pellets of spent catalyst B were allowed to contact the combined deposition mixture for 3 minutes. The resulting pellets of intermediate catalyst B were then centrifuged at 500 rpm for 2 minutes to remove excess liquid. The centrifuged intermediate catalyst B pellets were placed in a vibrating shaker and dried in flowing air at 250° C. for 5½ minutes.

The final composition of the rejuvenated catalyst B pellets was determined. The rejuvenated catalyst B pellets comprised 21.9 w % Ag, based on the total weight of rejuvenated catalyst B and 674 ppm of extracted Cs/g of rejuvenated catalyst. The silver and extracted cesium content of the rejuvenated catalyst B pellets were determined as described above. The rejuvenated catalyst B pellets also comprised the following, calculated on the basis of pore volume impregnation of the spent catalyst B: 2.0 µmole Re/g of rejuvenated catalyst B; 0.60 µmole W/g of rejuvenated catalyst B; and, 15 µmole extracted LiOH/g of rejuvenated catalyst B.

The results are given in the following Table, along with the composition of the Additivated Comparative Catalyst of Example 3:

| | Ag w % | Re, µmol/g | W, µmol/g | Li, µmol/g | Cs, ppm |
|---|---|---|---|---|---|
| Additivated Comparative Catalyst | 23.0 | 2.0 | 0.6 | 15 | 650 |
| Rejuvenated Catalyst A | 23.5 | 2.0 | 0.6 | 15 | 639 |
| Rejuvenated Catalyst B | 21.86 | 2.0 | 0.6 | 15 | 674 |

As seen from the foregoing, the silver and cesium content of Catalyst A and B increased substantially as a result of the rejuvenation process. Referring to the Table in Example 4 for the spent epoxidation catalyst, the silver content of Rejuvenated Catalyst A increased by 9 w %, and the silver content of Rejuvenated Catalyst B increased by 8.2 w %. The extracted cesium from Rejuvenated Catalyst A increased by 567 ppm and the extracted cesium from Rejuvenated Catalyst B increased by 629 ppm, both based on the extraction of spent Catalyst A after washing. Based on the cesium content of the respective spent catalysts before washing, the extracted cesium from Rejuvenated Catalyst A increased by 313 ppm and the extracted cesium from Rejuvenated Catalyst B increased by 280 ppm.

Performance Testing

Test Procedure

The various catalysts were tested to determine their catalytic properties, such as, selectivity and activity.

The following test procedure was used in the following Examples. The catalyst was crushed to 14 to 20 mesh size. 3 to 5 g of the crushed catalyst was loaded into a ¼ inch stainless steel U-shaped tube. The tube was immersed in a molten metal bath (heat medium) and the ends were connected to a gas flow system. The weight of catalyst used and the inlet gas flow rate were adjusted to give the specified gas hourly space velocity in normal liter/liter/hour (Nl/l/h), as calculated for uncrushed catalyst. As the catalyst packing density and silver loading changed, the amount of catalyst loaded in the test reactor was changed.

EXAMPLE 6

The spent comparative catalyst (control) was tested for its ability to produce ethylene oxide from a feed containing ethylene and oxygen.

The gas hourly space velocity was 3300 Nl/l/h. The catalyst loading was 4.90 grams. The gas flow was 16.9 Nl/l/h. The inlet gas pressure was 1550 kPa. The results are given in the summary Table found in Example 11.

EXAMPLE 7

Testing of Spent Catalyst A

In this Example, the testing gas mixture passed through the catalyst bed consisted of 30% v ethylene, 8% v oxygen, 5% v carbon dioxide, 57% v nitrogen and 2.5 parts by million by volume (ppmv) ethyl chloride. Temperature was kept constant at 245° C. for 4 hours and then adjusted for the catalyst to stabilize and achieve 3.09 vol. % ethylene oxide (EO) production, based on the total volume of the testing gas. The catalyst loading was 3.93 grams. The gas flow was 16.9 Nl/l/h. The inlet gas pressure was 1550 kPa. The results are given in the summary Table found in Example 11.

EXAMPLE 8

Testing of Spent Catalyst B

Prior to startup the catalyst was pre-treated for 3 hours with nitrogen at 260° C. Then the testing gas mixture was introduced. The testing gas mixture passed through the catalyst bed consisted of 30% v ethylene, 8% v oxygen, 5% v carbon dioxide, 57% v nitrogen and 2.5 to 7.0 parts by million by volume (ppmv) ethyl chloride. The temperature was kept constant at 260° C. for 4 hours and then adjusted for the catalyst to stabilize and achieve 3.09 vol. % EO production. The ethyl chloride concentration was varied to obtain maximum selectivity. The catalyst loading was 4.20 g. The gas flow was 16.9 Nl/l/h. The inlet gas pressure was 1550 kPa. The results are given in the summary Table found in Example 11.

EXAMPLE 9

Testing of Additivated Comparative Catalyst

The testing gas mixture which was passed through the catalyst bed consisted of 30% v ethylene, 8% v oxygen, 5% v carbon dioxide, 57% v nitrogen and 2.5 to 7 parts by million by volume (ppmv) ethyl chloride. Temperature was kept constant at 245° C. for 1 hour, 255° C. for 1 hour, and 255° C. for 1 hour, and then adjusted for the catalyst to stabilize and achieve 3.09 vol. % EO production. Ethyl chloride concentration was varied to obtain maximum selectivity. The catalyst loading was 4.90 grams. The gas flow was 16.9 Nl/l/h. The inlet gas pressure was 1550 kPa. The results are given in the summary Table found in Example 11.

EXAMPLE 10

Testing of Rejuvenated Catalyst A

Prior to startup, rejuvenated catalyst A was pre-treated for 3 hours with a gas mixture of 11.4% oxygen, 7% carbon dioxide and 81.6% nitrogen at 280° C. Then the reactor was cooled down to 240° C. and testing gas mixture was introduced. The testing gas mixture passed through the catalyst bed consisted of 30% v ethylene, 8% v oxygen, 5% v carbon dioxide, 57% v nitrogen, and 2.5 to 7.0 parts by million by volume (ppmv) ethyl chloride. Temperature was adjusted for the catalyst to stabilize and achieve 3.09 vol. % EO production. Ethyl chloride concentration was varied to obtain maximum selectivity. The catalyst loading was 4.48 g. The gas flow was 16.9 Nl/l/h. The inlet gas pressure was 1550 kPa. The results are given in the summary Table found in Example 11.

EXAMPLE 11

Testing of Rejuvenated Catalyst B

Prior to startup, the catalyst was pre-treated for 3 hours with a gas mixture of 11.4% oxygen, 7% carbon dioxide and 81.6% nitrogen at 280° C. Then the reactor was cooled down to 240° C. and testing gas mixture was introduced. The testing gas mixture passed through the catalyst bed consisted of 30% v ethylene, 8% v oxygen, 5% v carbon dioxide, 57% v nitrogen and 2.5 to 7.0 parts by million by volume (ppmv) ethyl chloride. Temperature was adjusted for the catalyst to stabilize and achieve 3.09 vol. % EO production. Ethyl chloride concentration was varied to obtain maximum selectivity. The catalyst loading was 4.80 g. The gas flow was 16.9 Nl/l/h. The inlet gas pressure was 1550 kPa.

The results for Examples 6-11 are given in the following Table:

|  | Sel % | Act ° C. |
|---|---|---|
| Spent Comparative Catalyst | 71.9 | 298 |
| Spent Catalyst A | 75.0 | 254 |
| Spent Catalyst B | 77.0 | 291 |
| Additivated Comparative Catalyst | 48.2 | 290* |
| Rejuvenated Catalyst A | 87.9 | 255 |
| Rejuvenated Catalyst B | 87.9 | 261 |

*EO concentration of 1.81% was achieved before the catalyst went into runaway

The foregoing results indicate that depositing a combination of components comprising rhenium, tungsten, lithium, and cesium onto a spent comparative catalyst was not effective to rejuvenate the comparative catalyst. However, depositing additional silver together with rhenium, tungsten, lithium, and cesium was very effective in rejuvenating both spent catalyst A and spent catalyst B.

EXAMPLE 12

An experiment was performed to assess the impact of the rejuvenation process on the activity of an extensively aged spent catalyst comprising α-alumina doped with silver, lithium, and cesium. The spent catalyst had a cumulative alkylene oxide production of 0.16 kT/m$^3$ of catalyst or more. A composite of four mid-top tube sections comprising from 190 g to 195 g of material were combined and tumbled for 25 minutes to thoroughly mix the cuts. 450 g of the composite was washed with a flow of 0.8 l/min of 95° C. water for 5 hours to remove water-soluble components. The washed composite was then dried at 120° C. for 2 hours.

Samples of the dried composite were impregnated with 4.0 w %, 8.0 w %, or 12.0 w % silver, based on the weight of the washed composite. The samples were impregnated using the stock silver solution of Example 2 and the procedure described in Example 4. Each of the impregnating solutions also comprised cesium in varying amounts and lithium in an amount of 40 μmol/g, both based on the weight of the rejuvenated catalyst, calculated based on pore volume impregnation of the spent epoxidation catalyst. The varying cesium levels are indicated in the Table, below.

The rejuvenated epoxidation catalysts and the spent epoxidation catalyst (as received from the customer) were subjected to a test procedure. The testing gas mixture consisted of 30% v ethylene, 8% v oxygen, 5% v carbon dioxide, 57% v nitrogen, and 2.5 parts per million by volume (ppmv) ethyl chloride. The gas hourly space velocity (GHSV) was 3300 hr$^{-1}$. The workrate was 200 kg/m$^3$/hr (12.5 lbs/ft$^3$/hr). The unit "kg/m$^3$/hr" refers to kilograms of ethylene oxide produced per cubic meter of epoxidation catalyst per hour, as calculated for uncrushed catalyst. The pressure was maintained at 14.7 barg (210 psig). The total gas flowrate was 281 cc/min. The temperature was adjusted for the catalyst to stabilize and achieve 3.1 vol. % EO production.

The results are given in the following Table:

|  | Selectivity (%) | Temperature (° C.) |
|---|---|---|
| Fresh Catalyst | 80.8 | 223 |
| Spent Catalyst | 75.7 | 261 |
| 8% w added silver: | | |
| C: 420 ppmw Cs | 79.0 | >230 |
| D: 470 ppmw Cs | 79.0 | 230 |
| E: 520 ppmw Cs | 79.5 | >240 |

-continued

|  | Selectivity (%) | Temperature (° C.) |
|---|---|---|
| F: 570 ppmw Cs | 78.0 | >240 |
| G: 320 ppmw Cs | 78.3 | 229 |
| H: 370 ppmw Cs | 78.9 | 229 |
| 12% w added silver: | | |
| I: 370 ppmw Cs | 80.6 | 224 |
| J: 420 ppmw Cs | 80.6 | 227 |
| K: 470 ppmw Cs | 80.6 | 230 |
| L: 520 ppmw Cs | 80.0 | 234 |
| 4% w added silver: | | |
| M: 370 ppmw Cs | 79.7 | 230 |
| N: 420 ppmw Cs | 79.7 | 231 |
| O: 470 ppmw Cs | 79.9 | 231 |
| P: 520 ppmw Cs | 78.6 | 237 |

The selectivity and temperature shown for "fresh catalyst" are averages for fresh catalyst production. The rejuvenated epoxidation catalysts comprising 12 w % additional Ag and containing from 370 ppmw to 520 ppmw rejuvenating Cs performed as well as fresh catalyst.

EXAMPLE 13

Rejuvenated catalyst comprising 12 w % additional Ag and 370 ppmw rejuvenating Cs (Catalyst "I" in Example 12) was subjected to a high severity microreactor (HSM) test to beyond 100 Mlbs/ft$^3$ of catalyst cumulative production. The testing gas mixture passed through the reactor consisted of 30% v ethylene, 8% v oxygen, 5% v carbon dioxide, 57% v nitrogen, and 5.6 parts by million by volume (ppmv) ethyl chloride. The gas hourly space velocity (GHSV) was 25000 hr$^{-1}$. The oxygen conversion was 25%, which is equivalent to ethylene oxide production of approximately 800 kg/m$^3$/hr (50 lbs/ft$^3$/hr), based on the loading density of whole catalyst pellets in a commercial reactor tube. The pressure was maintained at 14.7 barg (210 psig).

Figure 1:
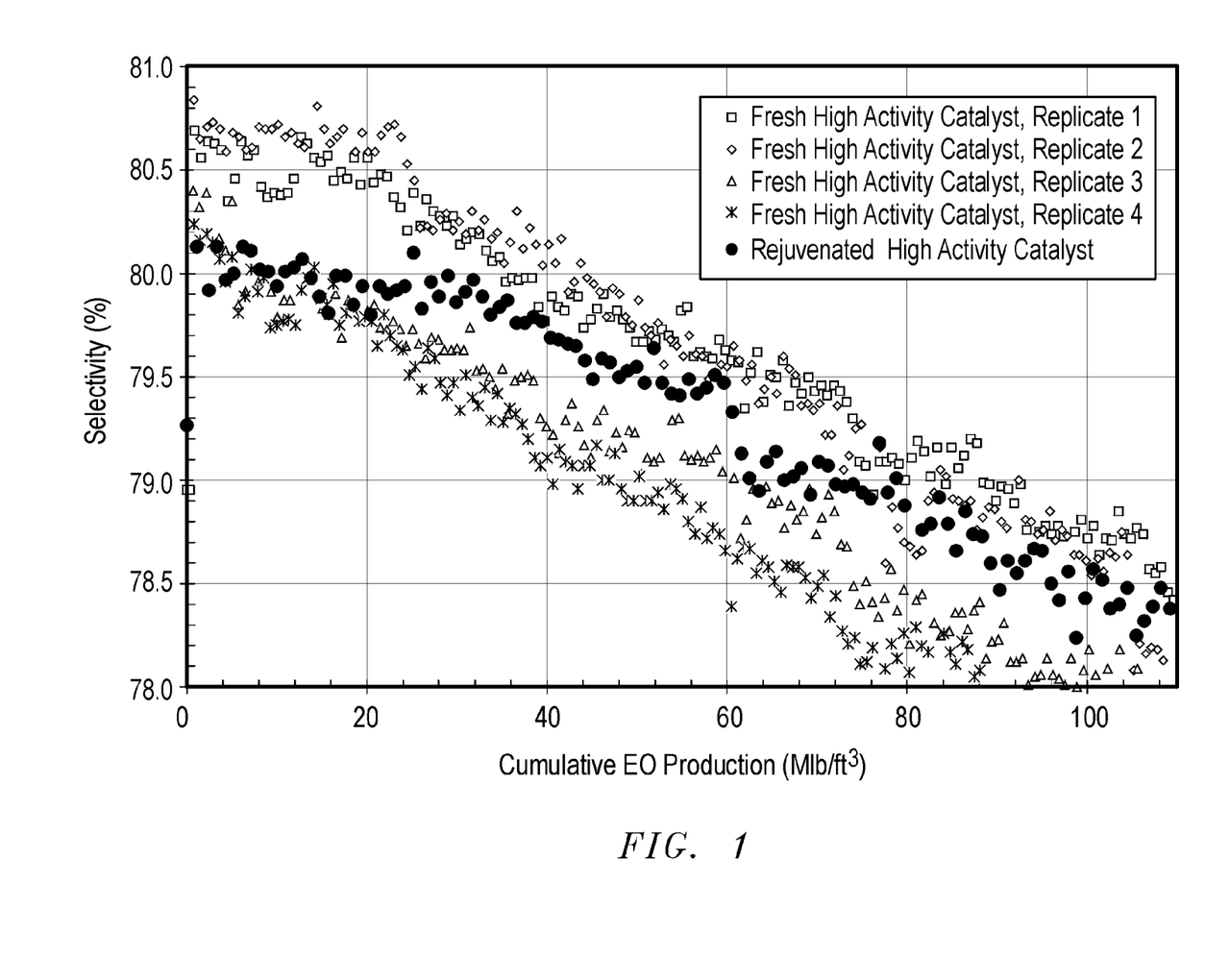
FIG. 1 is a graph of cumulative ethylene oxide production (Mlb/$ft^3$) versus selectivity (%) for four runs of the fresh catalyst and for the rejuvenated catalyst in Example 13. 100 Mlb/$ft^3$ of the catalyst=1.6 kT/$m^3$ of the catalyst.
Figure 2:
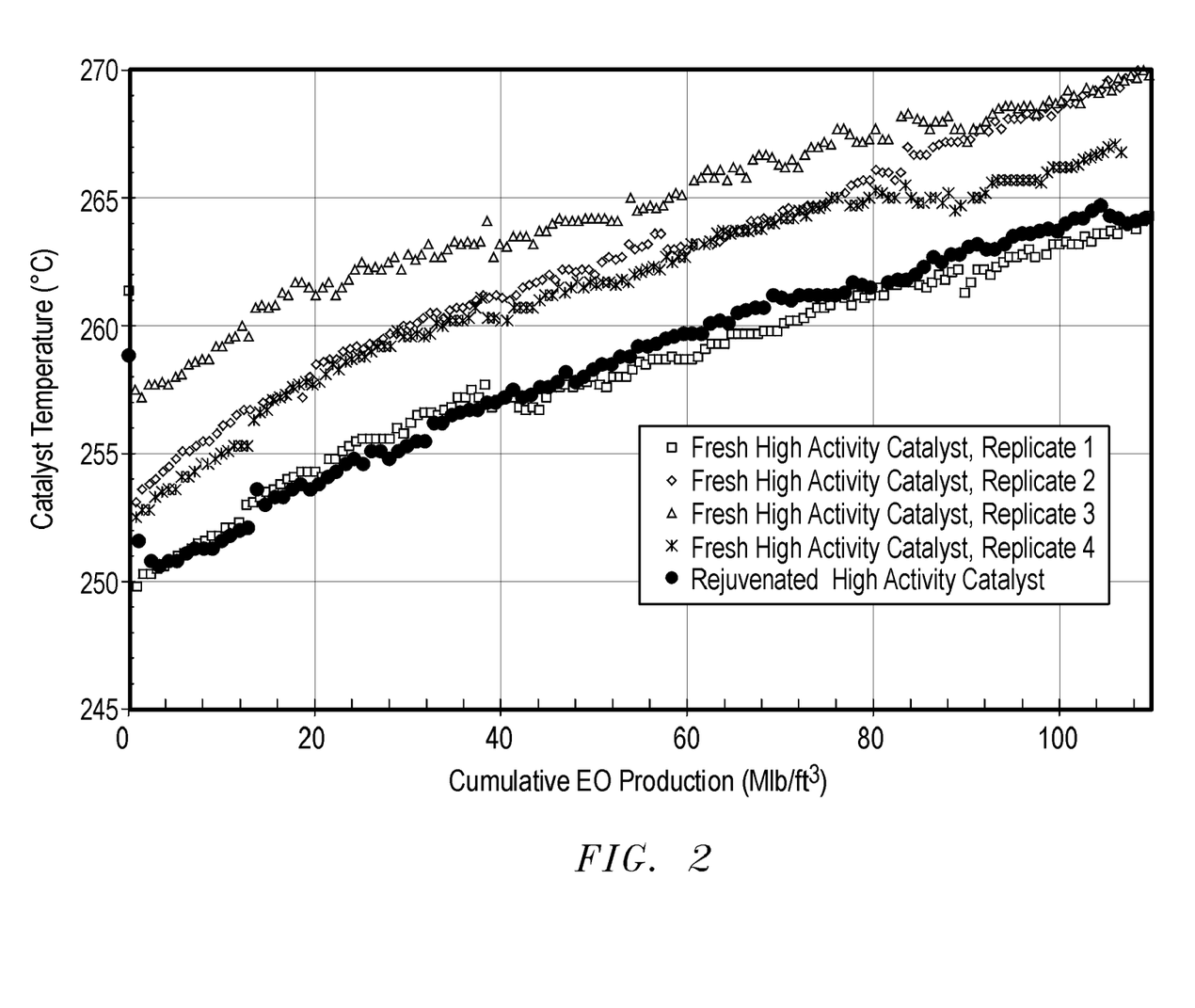
FIG. 2 is a graph of cumulative ethylene oxide production (Mlb/$ft^3$ of the catalyst) versus catalyst temperature (° C.) for four runs of the fresh catalyst and for the rejuvenated catalyst in Example 13.

FIG. 1 is a graph of cumulative ethylene oxide production (Mlb/ft$^3$ of catalyst) versus selectivity (%) for four runs of the fresh catalyst and for the rejuvenated high activity catalyst. FIG. 2 is a graph of cumulative ethylene oxide production (Mlb/ft$^3$ of catalyst) versus catalyst temperature (° C.) for four "identical" runs of the fresh catalyst, to provide an indication of the inherent statistical variability of the testing procedure, and for the rejuvenated high activity catalyst.

With respect to both selectivity decline and activity decline rates, the rejuvenated high activity catalyst performed the same as fresh high activity catalyst within the experimental scatter of the data.

Persons of ordinary skill in the art will recognize that many modifications may be made to the embodiments described herein. The embodiments described herein are meant to be illustrative only and should not be taken as limiting the invention, which will be defined in the claims.

We claim:

1. A process for preparing a rejuvenated epoxidation catalyst, the process comprising:
   providing a quantity of spent epoxidation catalyst comprising silver and having a cumulative alkylene oxide production of 0.16 kT/m3 of the spent epoxidation catalyst or more; and,
   depositing silver on the spent epoxidation catalyst in an amount of 1% w or more, based on the weight of the spent epoxidation catalyst, without the prior removal of any silver from the spent epoxidation catalyst.

2. The process of claim 1 further comprising depositing the silver in an amount of 4% w or more, based on the weight of the spent epoxidation catalyst.

3. The process of claim 1 further comprising depositing the silver in an amount of 5% w or more, based on the weight of the spent epoxidation catalyst.

4. The process of claim 1 further comprising depositing the silver in an amount of 12% w or more, based on the weight of the spent epoxidation catalyst.

5. The process of claim 1 wherein the silver deposited is cationic silver and the process further comprises reducing the cationic silver.

6. The process of claim 1 further comprising depositing a quantity of rejuvenating rhenium on the spent epoxidation catalyst.

7. The process of claim 6 further comprising depositing on the spent epoxidation catalyst a quantity of one or more rejuvenating copromoter components comprising an element selected from the group consisting of tungsten, chromium, molybdenum, sulfur, phosphorus, boron, and mixtures thereof.

8. The process of claim 1 further comprising depositing on the spent epoxidation catalyst a quantity of one or more rejuvenating further elements selected from the group consisting of nitrogen, fluorine, alkali metals, alkaline earth metals, titanium, hafnium, zirconium, vanadium, thallium, thorium, tantalum, niobium, gallium, germanium, and mixtures thereof.

9. The process of claim 8 wherein the rejuvenating further element comprises one or more rejuvenating alkali metals selected from the group consisting of lithium, potassium, cesium, and mixtures thereof.

10. The process of claim 9 wherein the rejuvenating alkali metal comprises cesium in an amount of 0.1 to 50 mmole/kg of the rejuvenated epoxidation catalyst.

11. The process of claim 1 further comprising washing the spent epoxidation catalyst before depositing the silver on the spent epoxidation catalyst.

12. The process of claim 6 comprising depositing the rejuvenating rhenium in a quantity of from 0.1 to 20 mmole/kg of the rejuvenated epoxidation catalyst.

13. The process of claim 7 comprising depositing the rejuvenating copromoter in a quantity of from 0.1 to 20 mmole/kg of the rejuvenated epoxidation catalyst.

14. The process of claim 9 wherein the rejuvenating alkali metal comprises lithium in a quantity of from 1 to 100 mmole/kg of the rejuvenated epoxidation catalyst.

15. The process of claim 1 wherein the spent epoxidation catalyst has a cumulative alkylene oxide production of 1 kT/m$^3$ of the spent epoxidation catalyst or more.

16. The process of claim 1 further comprising:
   depositing the silver in an amount of 12% w or more, based on the weight of the spent epoxidation catalyst;
   depositing an amount of rejuvenating cesium which produces from 300 ppmw to 600 ppmw extracted cesium; and,
   depositing lithium in an amount of 40 mmole/kg of the rejuvenated epoxidation catalyst, calculated by pore volume impregnation of the spent epoxidation catalyst.

17. A process of preparing rejuvenated epoxidation catalyst, the process comprising:
   providing a quantity of spent epoxidation catalyst comprising silver and having a cumulative alkylene oxide production of 0.16 kT/m$^3$ of the spent epoxidation catalyst or more;
   depositing on the spent epoxidation catalyst:

silver in an amount of 1% w or more, based on the weight of the spent epoxidation catalyst, without the prior removal of any silver from the spent epoxidation catalyst;
a quantity of rejuvenating rhenium;
a quantity of one or more rejuvenating copromoter components comprising an element selected from the group consisting of tungsten, chromium, molybdenum, sulfur, phosphorus, boron, and mixtures thereof; and,
a quantity of one or more rejuvenating further elements comprising one or more alkali metals selected from the group consisting of lithium, potassium, cesium, and mixtures thereof.

18. The process of claim 17 further comprising depositing the silver in an amount of 5% w or more, based on the weight of the spent epoxidation catalyst.

19. The process of claim 17 further comprising depositing the silver in an amount of 12% w or more, based on the weight of the spent epoxidation catalyst.

20. The process of claim 17 comprising
depositing rejuvenating cesium in an amount of from 0.1 to 50 mmole/kg of the rejuvenated epoxidation catalyst;
depositing rejuvenating rhenium in a quantity of from 0.1 to 20 mmole/kg of the rejuvenated epoxidation catalyst;
depositing rejuvenating copromoter in a quantity of from 0.1 to 20 mmole/kg of the rejuvenated epoxidation catalyst; and,
depositing rejuvenating lithium in an amount of from 1 to 100 mmole/kg of the rejuvenated epoxidation catalyst.

21. The process of claim 17 further comprising washing the spent epoxidation catalyst before depositing the amount of silver on the spent epoxidation catalyst.

22. The process of claim 17 wherein the spent epoxidation catalyst has a cumulative alkylene oxide production of 1 kT/m$^3$ of the spent epoxidation catalyst or more.

23. The process of claim 17 wherein the spent epoxidation catalyst exhibits a 10% or greater reduction in selectivity compared to the initial selectivity under the initial conditions.

24. The process of claim 17 comprising depositing on the spent epoxidation catalyst:
the silver in an amount of 8% w or more, based on the weight of the spent epoxidation catalyst;
the rejuvenating cesium in an amount which produces from 300 ppm to 1000 ppm extracted cesium;
the rejuvenating rhenium in an amount of from 1 mmole/kg to 5 mmole/kg of the rejuvenated epoxidation catalyst, calculated by pore volume impregnation of the spent epoxidation catalyst;
the rejuvenating tungsten in an amount of from 0.5 mmole/kg to 5 mmole/kg of the rejuvenated epoxidation catalyst, calculated by pore volume impregnation of the spent epoxidation catalyst; and,
the rejuvenating lithium in an amount of from 10 mmole/kg to 40 mmole/kg of the rejuvenated epoxidation catalyst, calculated by pore volume impregnation of the spent epoxidation catalyst.

25. The process of claim 17 comprising depositing on the spent epoxidation catalyst:
the silver in an amount of 8% w, based on the weight of the spent epoxidation catalyst;
the rejuvenating cesium in an amount which produces from 600 ppm to 650 ppm extracted cesium;
the rejuvenating rhenium in an amount of 2 mmole/kg of the rejuvenated epoxidation catalyst, calculated by pore volume impregnation of the spent epoxidation catalyst;
the rejuvenating tungsten in an amount of 0.6 mmole/kg of the rejuvenated epoxidation catalyst, calculated by pore volume impregnation of the spent epoxidation catalyst; and,
the rejuvenating lithium in an amount of 15 mmole/kg of the rejuvenated epoxidation catalyst, calculated by pore volume impregnation of the spent epoxidation catalyst.

26. A process for the epoxidation of one or more olefins using rejuvenated epoxidation catalyst, the process comprising:
providing a quantity of spent epoxidation catalyst comprising silver and having a cumulative alkylene oxide production of 0.16 kT/m$^3$ of the spent epoxidation catalyst or more;
depositing silver on the spent epoxidation catalyst in an amount of 1% w or more, based on the weight of the spent epoxidation catalyst, without the prior removal of any silver from the spent epoxidation catalyst; and
reacting a feed comprising the one or more olefins and oxygen in the presence of the rejuvenated epoxidation catalyst to produce olefin oxide.

27. The process of claim 26 wherein the one or more olefins comprise ethylene.

28. The process of claim 26 comprising depositing the silver in an amount of 5% w or more, based on the weight of the spent epoxidation catalyst.

29. The process of claim 26 comprising depositing the silver in an amount of 12% w or more, based on the weight of the spent epoxidation catalyst.

30. The process of claim 26 further comprising depositing on the spent epoxidation catalyst one or more materials selected from the group consisting of:
rejuvenating rhenium;
one or more rejuvenating copromoter components comprising an element selected from the group consisting of tungsten, chromium, molybdenum, sulfur, phosphorus, boron, and mixtures thereof; and
one or more rejuvenating alkali metals selected from the group consisting of lithium, potassium, cesium, and mixtures thereof.

31. The process of claim 26 wherein the spent epoxidation catalyst has a cumulative alkylene oxide production of 1 kT/m$^3$ of the spent epoxidation catalyst or more.

* * * * *